United States Patent
Burgi et al.

(10) Patent No.: US 9,562,915 B2
(45) Date of Patent: *Feb. 7, 2017

(54) PORTABLE ELECTRONIC DEVICE WITH BREATH ANALYZER

(71) Applicant: Sensirion AG, Stafa (CH)

(72) Inventors: Lukas Burgi, Zurich (CH); Felix Mayer, Stafa (CH); Frank Roeck, Wil (CH)

(73) Assignee: Sensirion AG, Stafa (CH)

(*) Notice: Subject to any disclaimer, the term of this patent is extended or adjusted under 35 U.S.C. 154(b) by 0 days.

This patent is subject to a terminal disclaimer.

(21) Appl. No.: 14/160,829

(22) Filed: Jan. 22, 2014

(65) Prior Publication Data

US 2014/0234172 A1    Aug. 21, 2014

(30) Foreign Application Priority Data

Jan. 31, 2013    (EP) .................................... 13405018

(51) Int. Cl.
| | | |
|---|---|---|
| *G01N 33/98* | (2006.01) | |
| *G01N 33/497* | (2006.01) | |
| *A61B 5/087* | (2006.01) | |
| *A61B 5/08* | (2006.01) | |

(52) U.S. Cl.
CPC .......... *G01N 33/98* (2013.01); *G01N 33/4972* (2013.01); *A61B 5/082* (2013.01); *A61B 5/087* (2013.01); *G01N 33/497* (2013.01)

(58) Field of Classification Search
CPC ... G01N 33/497; G01N 33/98; H04M 2250/12

USPC .............................................. 422/84; 73/23.3
See application file for complete search history.

(56) References Cited

U.S. PATENT DOCUMENTS

| | | | |
|---|---|---|---|
| 5,531,225 A | 7/1996 | Nawata et al. | |
| 8,183,527 B2 | 5/2012 | Taguchi et al. | |
| 9,456,749 B2* | 10/2016 | Roeck | .................. G01N 33/497 |
| 2007/0093725 A1 | 4/2007 | Shaw | |
| 2009/0164141 A1 | 6/2009 | Lee | |
| 2010/0188232 A1 | 7/2010 | Lambert et al. | |
| 2011/0307208 A1 | 12/2011 | Graf et al. | |
| 2012/0231841 A1 | 9/2012 | Niederberger et al. | |
| 2012/0272713 A1* | 11/2012 | Kountotsis et al. | ........... 73/23.3 |

(Continued)

FOREIGN PATENT DOCUMENTS

| | | |
|---|---|---|
| EP | 1772725 | 4/2007 |
| EP | 1942345 | 7/2008 |

(Continued)

*Primary Examiner* — Lyle Alexander
*Assistant Examiner* — Bryan Kilpatrick
(74) *Attorney, Agent, or Firm* — Cooper & Dunham LLP

(57) ABSTRACT

A breath analyzer is described with at least one chemical sensor sensitive to the concentration of a component in a sample of exhaled breath including a compensator for compensating for the effect of variations in the amount of exhaled breath between the user and the sensor location with the chemical sensor being integrated into a portable electronic device, particularly with the sensor being located in an air duct with an opening to the exterior of the housing of the analyzer with the total area of the opening being sufficiently small to restrict effectively mass transport between the exterior and the sensor and/or wherein the compensation includes the compensation for different responses of sensors.

10 Claims, 4 Drawing Sheets

(56) References Cited

U.S. PATENT DOCUMENTS

2013/0192338 A1\* 8/2013 Mayer et al. ............... 73/23.3
2014/0228698 A1\* 8/2014 Roeck et al. ............... 600/532

FOREIGN PATENT DOCUMENTS

| WO | 9519563 | 7/1995 |
| WO | 2008108714 | 9/2008 |
| WO | WO 2012097459 A1 \* | 7/2012 |
| WO | 2012100362 | 8/2012 |

\* cited by examiner

PORTABLE ELECTRONIC DEVICE WITH BREATH ANALYZER

FIELD OF THE INVENTION

The present invention relates to a breath analyzing device.

BACKGROUND OF THE INVENTION

Portable or mobile devices originally introduced as mobile phones or electronic agendas become more and more ubiquitous. As the processing power of their internal processors grows and equally the bandwidth for communication with remote or stationary processors, such portable devices take on more and more the role of multi-purpose tools available to consumers and specialist users alike.

It has been recognized that portable devices can benefit from the presence of sensors capable of providing a chemical analysis of materials brought into contact or the vicinity of the device. Whilst there are many possible applications for such sensors, it suffices to consider for example the analysis of air surrounding the portable device. Such an analysis can be useful for multiple purposes such as testing for hazardous gases, breath analysis for general medical purposes or driving fitness, and the like.

Specialized portable devices for testing the breath for alcohol are well known and widely used by law enforcing authorities as preliminary test kits for blood alcohol concentration (BAC). One conventional method to measure BAC of a person requires the person to fully exhale into a mouthpiece coupled to an apparatus that uses a fuel cell sensor to measure the ethanol vapor concentration in the exhaled breath emerging near the end of the exhalation.

However, some people find this unpleasant and generally a mouthpiece is not acceptable in mobile devices of the present invention, which are typically designed to have multiple purposes not necessarily restricted to solely breath analysis. Other conventional methods and apparatus for measuring BAC do not require a person to exhale into a mouthpiece, but rely generally on a valve to route a second source of air without exhaled breath or without ethanol gas to serve as a baseline for determining ethanol gas concentration. Other methods rely on complicated signal analysis techniques that compare waveforms from an ethanol gas detector and a carbon dioxide gas detector.

It has been proposed to equip vehicles with blood alcohol concentration (BAC) sensors to estimate the BAC of a person attempting to operate a vehicle based on the concentration of ethanol gas in the breath of the person. Such attempts are described for example in the U.S. Pat. Nos. 5,531,225 A, 8,183,527 B, the published United States patent application US 2010/0188232 and other documents. These devices are typically designed for the specific purpose of analyzing the breath for alcohol content and form a permanent fixture of the car they are installed in.

It has further been recognized that devices which receive a mixture of breath and surrounding air require compensation for the dilution caused by the surrounding air. As described in the above cited documents, the compensation can be done using for example—in parallel to such devices—humidity measurements, other chemical measurements (e.g. CO2, O2 concentrations) or temperature measurements.

Humidity sensors for mobile applications are described for example in the published United States patent application US 2012/231841 and ways of manufacturing miniaturized sensors as MEMS devices with CMOS connections and circuitry are described for example in the published international patent application WO 2012/100362 A1. Metal-oxide sensors with integrated heaters are described for example in the international patent application WO 95/19563.

For general purpose portable devices the problem of making an accurate measurement and compensating for example for the effects of dilution becomes compounded by the dimension of the opening or openings through which the sensor receives the sample of exhaled air. It is therefore seen as an object of the present invention to improve the accuracy of the measurement of alcohol concentration or other components in a sample of exhaled breath using a multi-purpose portable electronic device.

SUMMARY OF THE INVENTION

Hence, according to a first aspect of the invention, there is provided a breath analyzer with at least one chemical sensor sensitive to the concentration of a component such as ethanol in a sample of exhaled breath including a compensator for compensating for the effect of variations in the amount of exhaled breath between the user and the sensor location with the chemical sensor being integrated into a portable electronic device, preferably with telecommunication capabilities to allow for data and/or voice communication via private or public networks.

In a particularly preferred embodiment the chemical sensor is enclosed in the housing of the portable device within an air duct with an opening cache exterior of the housing and with the total area of the opening being sufficiently small to act as restriction to diffusion.

The diffusion restriction can be regarded as any opening acting as an impedance to an instantaneous or nearly instantaneous establishment of an equilibrium of the air in front of and behind the opening. Thus any changes in the composition of the air propagate into the housing with a delay. Under the normal operating conditions of a typical mobile device, this delay exceeds the time during which the air is moved and exchanged around the device or the acceptable time limit for a user to receive a result of the measurement. Without compensation a measurement would thus result in a significantly lower value than the true value.

The opening itself can be a dedicated opening thus exclusively connecting the chemical sensor to the outside. However, given that the manufacturers of portable electronic devices strive to maintain the housing as a good protection against humidity and water, it is seen as advantageous that the opening is shared with at least one further component of the portable device requiring a similar connection to the exterior, such as a loudspeaker, a microphone or a camera. The opening can further be protected by a grill or a membrane to prevent bigger particles or unwanted components of the air from entering or blocking the duct. The area of the opening is thus best restricted to 100 square millimeters or less, preferably less than 25 square millimeters and even more preferred to less than 10 square millimeters. The duct acts as confinement for the air inside the housing and can take the shape of a tube or channel formed as part of the housing or as a separate part connected to an opening in the housing. It can be a single straight or curved duct.

In a preferred embodiment of the invention, the compensator is connected to the output of at least one additional sensor sensitive to conditions in the space behind the opening to correct for dilution of exhaled breath by ambient air at the outside of the opening, such as a sensor for humidity, temperature, or an additional chemical sensor sensitive for example to carbon dioxide or oxygen concentrations.

In a preferred embodiment of the invention, the compensator includes a compensation for different characteristics, such as response times, of two or more sensors, for example by time shifting the measurement of one or more sensors or by using a filter which models the individual (impulse) response of one or more sensors. This aspect of the invention can be used for example to shorten the time required for a measurement. It can also be used independently for the above compensator, for example, in order to process chemical measurements from an array of different chemical sensors with different responses.

In a further preferred embodiment of the invention, the compensator determines a ratio of signals representative of changes in the humidity and signals representative of changes in the concentration of the component to correct for dilution of exhaled breath by ambient air at the outside of the opening.

In a further preferred embodiment of the invention, the compensator determines a value representative of the dew point to correct for dilution of exhaled breath by ambient air at the outside of the opening.

The compensator can further include values derived from measurement of ambient air made before or after the sampling of exhaled air to determine the compensation.

In a further preferred embodiment of the invention, the compensator corrects the signal representative of a concentration of the component or an initial or intermediate value as measured by the chemical sensor with a static or dynamic factor representing the geometry of the opening and/or the duct.

To increase the accuracy of the measurement the above devices for compensating for the dilution and for the geometry of the opening and/or the duct are best combined and applied both to a measurement.

The accuracy can be further increased by enabling the compensator devices to compensate for the characteristic of individual sensors, such as response times, as described above.

In a further preferred embodiment the compensator receives signals from a humidity sensor or other sensor located at a distance of less than 5 mm from the chemical sensor with both sensors located at a distance of less than 10 mm from the opening.

In a further preferred embodiment the compensator can be a specialized electronic circuit or a general purpose processing unit programmed to execute the functions of such a compensator.

The portable device can be a smart phone, a handheld computer, a laptop, an electronic reader, a tablet computer, a came controller, a pointing device, a photo or a video camera, digital music player, wrist watch, key fob, head set or a computer peripheral. Its housing is typically a shell of metal, glass, or plastic material and can be assembled as a unibody or from several parts. Enclosed in the housing are typically processors, rivers for parts such as screens, antennae, cameras, microphones and speakers as well as batteries to provide power to the device and its parts. A screen is typically arranged as a part of the housing or mounted behind a transparent window.

The chemical sensor may be understood as a sensor device for detecting one or even more properties of one or more analytes. It is preferably based on one of the following measurement principles:

The sensor can be based on a chemomechanical principle, in which a chemical reaction is transformed into weight increase, a surface acoustic wave, or into a cantilever resonance, for example. Alternatively, there may be thermal sensing concepts applied, e.g. by making use of pellistors which may serve as a catalytic thermal sensor in which heat is generated during combustion. Alternatively, the chemical sensor may rely on optical detection, such as in form of a microspectrometer, or an NDIR sensor, or may make use of electrochemical reactions such as being enabled by solid state electrolytes in combination with voltammetric, potentiometric, or conductometric measurement principles. Chemiresistors may also be used, such as conducting and carbon-loaded polymers, preferably in a low-temperature arena, or, more preferably, metal-oxide sensors such as tin oxide, tungsten oxide, gallium oxide, indium oxide, zinc oxide, which preferably may be applied in a high temperature environment. ISFET (ion-selective FET) may also be used, as well as chemocapacitors wherein it is preferred to use a polymer as active material.

The sensor includes the sensor material, preferably in form of a layer, also denoted as receptor layer, to which an analyte may bond to and as such modify an electrical property of the sensor material such as its electrical conductance, which principle preferably is applied in metal oxide chemical sensors, or an optical property such as its transmission rate. It can also include a plurality of different sensors or an array of similar sensors. In such a sensor array, each sensor cell may provide a layer of a material exhibiting different absorption characteristics such that each cell of the sensor array may specifically be sensitive to a different analyte and as such may enable the portable electronic device to detect the presence or absence or concentration of such analyte.

The above and other aspects of the present invention together with further advantageous embodiments and applications of the invention are described in further details in the following description and figures.

DETAILED DESCRIPTION

Figure 1A:
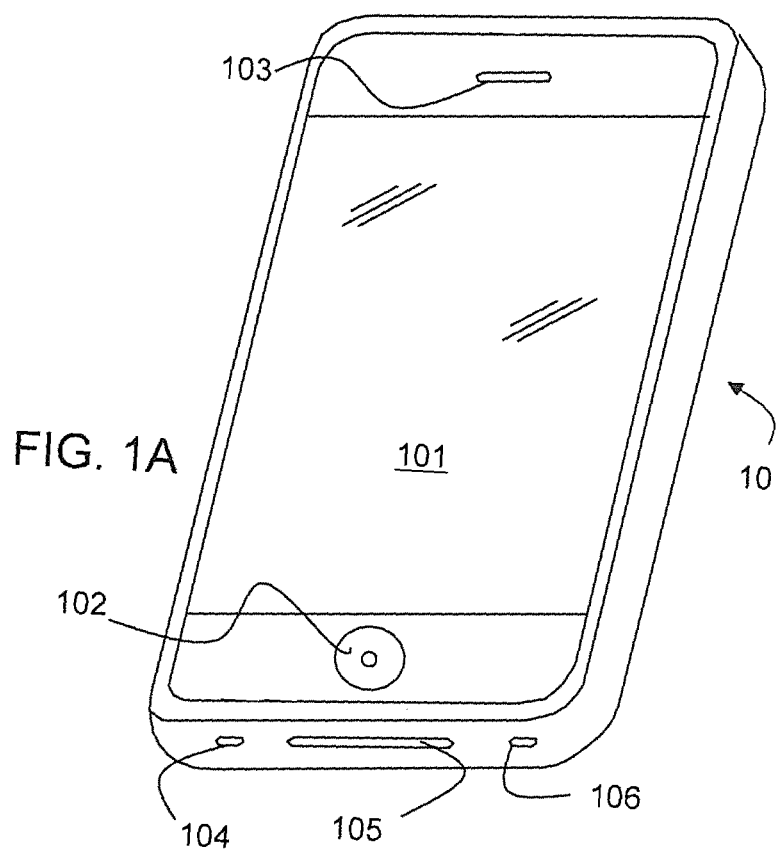
FIG. 1A is a perspective view of a portable electronic device.

The device of FIG. 1A is a portable electronic device such as a mobile phone. The housing 10 of the mobile phone includes a front side with a screen 101 and elements like buttons 102 to let a user interact with the phone. Also shown on the front side is an opening 103 for a loudspeaker. Further openings 104, 105 are located at a lower side wall of the housing 10. It is well known to mount components like microphones and loudspeakers behind such openings.

Figure 1B:
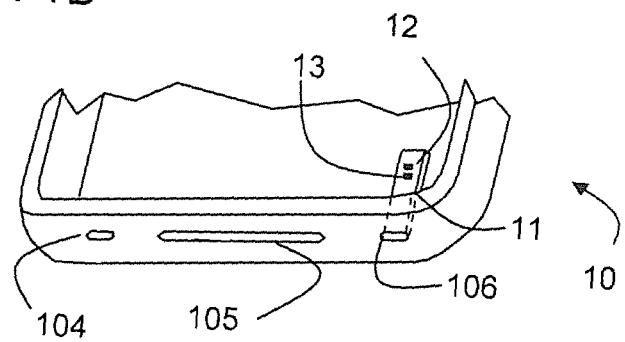
FIG. 1B is a schematic view into part of the housing of the device of FIG. 1A.

Another opening 106 is located at the lower side wall. As shown in FIG. 1B the opening 106 is linked to a tubular duct 11 passing through the interior of the housing. A chemical sensor 12 and a humidity sensor 13 are both mounted along the duct 11 such that the sensitive areas of both sensors are essentially exposed to air of the same composition entering the duct through the opening 106. The actual size and shape of the duct 11 depends on the volume available and the nature of the chemical sensor 12 and the humidity sensor 13, which can vary, but given the physical constraints of portable mobile devices the diameter of the opening is typically in the range of less than 2 mm and in the present example actually about 1 mm.

In the example the chemical sensor is a gas sensor using a metal-oxide layer mounted onto and integrated with a CMOS substrate. The metal-oxide used can be tin oxide, tungsten oxide, gallium oxide, indium oxide, or zinc oxide. For particular embodiments as described in further details below the sensor can also include a micro electro-mechanical system or MEMS type heat source integrated within the sensor. The sensor is integrated with its own CMS circuitry for control and readout. The physical dimensions of the board including the CMOS circuit and the MEMS sensor smaller than 5 mm×5 mm.

The chemical and humidity sensors 12, 13 can be manufactured as described for example in the cited application WO 2012/100362. The humidity sensor is best combined with a temperature sensor. Such sensors are commercially available, e.g. from Sensirion™ under trade name SHTC1. The SHTC1 sensor measures 2 mm×2 mm×0.8 mm. Both sensors can for example be mounted adjacent to each other in the duct 11. The humidity can also be measured by other types of sensors. It can for example be advantageous for a better integration of the device to use a second strongly humidity dependent metal oxide sensor for this measurement, whereby the second metal oxide sensor can be even integrated onto the same CMOS substrate as the chemical sensor 12. An enlarged schematic cross-section of the duct with the sensors is shown in FIG. 2.

Figure 2:
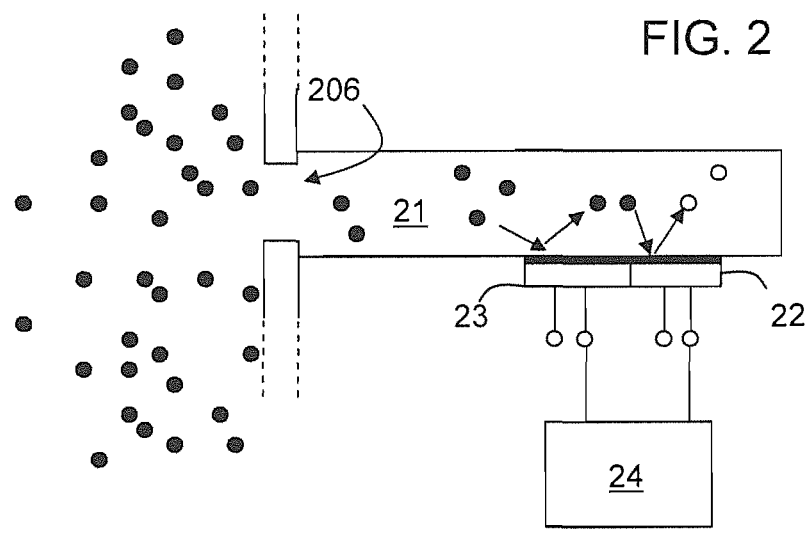
FIG. 2 is a schematic cross-section through a duct with a chemical sensor.

The cross-section of FIG. 2 shows an opening 206 in the housing and a duct 21 with the chemical sensor 22 and the humidity sensor 23. The output pins of both sensors are connected to a compensator 24, which is described in further detail below. A sample of gas is indicated by a cloud of black dots. The reaction which changes the resistance of the sensor is indicated by a transition from solid dots to white dots.

Replacing or in addition to the humidity sensor 23, a carbon dioxide sensor (e.g. a solid-state electrochemical sensor or a $CO_2$ sensor based on the measurement of the thermal conductivity) can be mounted within the duct 21.

Figure 3:
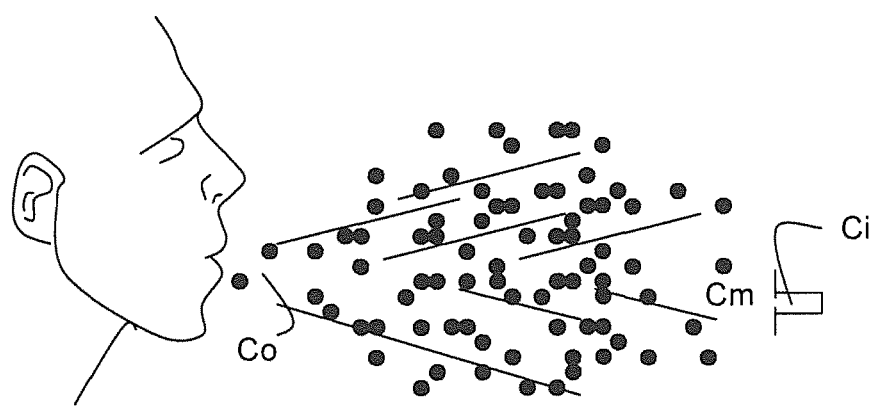
FIG. 3 illustrates a correction for dilution with ambient air.

A typical sampling scenario is illustrated in FIG. 3. The exhaled breath is assumed to contain the analyte, e.g. alcohol, acetone, NO, H2, or NH3, in a concentration Co. After exhaling the exhaled volume of breath mixes with ambient air with a different concentration of the same analyte, which is assumed to be zero corresponding for example to a situation where no alcohol is contained in the ambient air. The mixing of exhaled breath and ambient air results in a mixed concentration Cm, which is lower than the original concentration Co, on the outside of the small opening 206 of the duct 21 with the sensors. The ratio of the mixture depends on many factors such as volume of the exhaled air, its flow rate and the distance between the face and the mobile device, as well as the orientation of the opening with respect to the flow direction of the exhaled air.

These effects cause a first distortion of the measurement. A second distortion is introduced into the measuring process by the opening 206 to the duct 21. In the following it is assumed that the opening has the effect of increasing the time period required for the air inside the duct 21 to be in equilibrium with the air outside. In other words, an instant change of concentration Cm outside the opening 206 will only be reflected by a gradual change in the concentration Ci inside the duct 21. As indicated previously, the delay thus introduced by the opening 206 makes it very difficult to accurately measure an instantaneous change of concentration in the air around the device. In an everyday situation, there is often not sufficient time to wait until concentrations inside and outside the duct 21 are in equilibrium. The measurement has thus to be as close to an instantaneous measurement as possible to avoid the effects of for example air movement in the environment. In practical terms, it should be further considered that a user would expect a response from the measurement within less than 2 min or less, even within 1 min or less or even within 30 seconds of providing the sample. These constraints all limit the time available for the measurement.

The compensator of the present invention makes it possible to increase the accuracy of the measurement even within these limits. Depending on the desired degree of accuracy the compensator can be configured so as to compensate for the change from the original concentration Co to the concentration Cm after mixing or for the change of the concentration going from Cm to the concentration Ci within the duct 21 or both, i.e. for a change of the concentration from Co to Ci. The compensator provides a transformation between the different concentrations such that knowledge of the concentration Ci, which is measured by the chemical sensor, can be converted into Cm or Co.

In the case of an alcohol measurement the accurate knowledge of the concentration Co of alcohol in the breath can be easily converted into a BAC value using industry standard methods or conversions as prescribed by law enforcement authorities.

In accordance with the present example the compensator is designed to compensate for the two effects of variations in the amount of exhaled breath passing the barrier as described above. It is however worth noting that the compensator can be readily adapted to compensate for only one of the effects, in case the other is deemed to be not significant.

To compensate for example for the variation of the concentration of alcohol (EtOH) from Co to Cm, the compensator applies a correction in accordance with the equation [1]:

$$Pm(EtOH) = Po(EtOH) * (Pm(H2O) - Pa(H2O)) / (Po(H2O) - Pa(H2O)). \quad [1]$$

In equation [1] the partial pressure P is used as a measure of the concentration. As above, an index m denotes values of the mixed sample and an index o indicates the original value, whereas an index a is used for an ambient measurement in the absence of exhaled breath made prior or after the sampling measurement. The values for humidity or water concentration are indicated by H2O.

As shown the inverse of the ratio (Pm(H2O)−Pa(H2O))/(Po(H2O)−Pa(H2O)) or any equivalent thereof can be used to correct the measurement Pm(EtOH) so as to derive the true value. Po(EtOH) The partial pressures for water are measured by the humidity sensor. The ambient humidity is assumed to be constant for a time period around the time of the actual sampling. The partial pressure of water in the breath Po(H2O) is known to be very reproducible and corresponds to the vapour pressure of water at 34° C. The compensation factor derived from equation [1] can also be used as a threshold to reject measurements, for example in cases where the factor exceeds a certain value, beyond which the measurement is deemed to be inaccurate.

The above compensation for the effect of dilution can be used with molecules present in air other than water. It is thus possible to use essentially any component of the breath which has a known concentration in the breath and in the ambient air, whether being constant or not, to correct for the variation in concentration from Co to Cm. In particular it is known that the concentration of carbon dioxide or its counterpart oxygen in the exhaled breath is essentially constant. With the humidity sensor replaced by a sensor sensitive to either component, the above compensation can be applied in a similar manner by, for example, replacing equation [1] with the equation [1A]:

$$Po(EtOH)=Pm(EtOH)*Pm(CO2)/Po(CO2), \qquad [1A]$$

where Pm(CO2) is the measured carbon dioxide concentration and Po(CO2) is the known CO2 concentration in exhaled breath.

Figure 4:
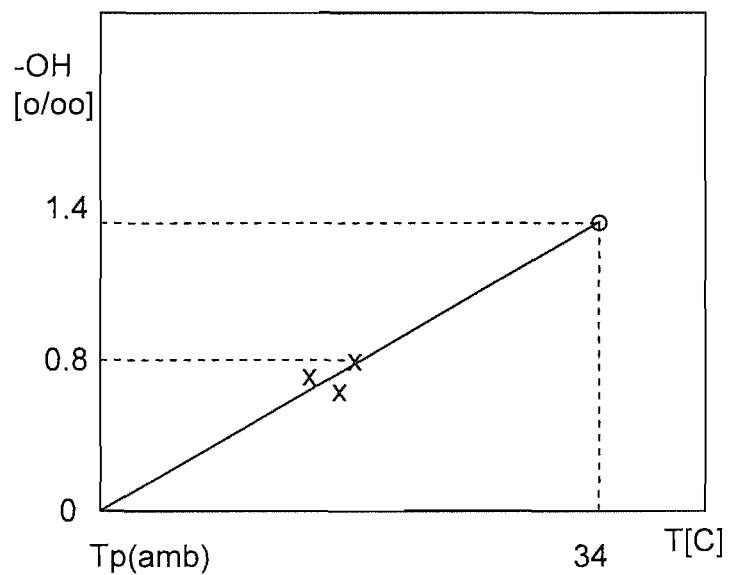
FIG. 4 illustrates a correction for dilution with ambient air using dew point determination.

In a variant of the above compensation, the compensator includes a dew point calculator. The operation of the dew point calculator is illustrated in FIG. 4. The dew point calculator uses a humidity measurement and temperature and converts the measurement into a dew point value. The dew point of human breath is known to be very reproducible and corresponds to 34 degrees Celsius.

As shown in FIG. 4 the concentration Cm of a component of the exhaled breath is assumed to lie on the straight line connecting the dew point of the ambient air, e.g. 15 degrees C. and zero concentration of the component with the dew point at 34 degrees Celsius and the unknown concentration Co. By extrapolating the line between 15 degrees C. and zero concentration and the measurements of Cm (indicated in FIG. 4 as "x") to 34 degrees C. it is possible to determine a value for the original concentration Co of the component in question. In the example the concentration is represented directly as BAC.

The compensator can be adapted to reject measurements based for example on a lower threshold, e.g. 20 degrees C., of the dew point (indicating a sample which is too diluted) or in case the measurements result in an extrapolated line having a gradient either higher or lower than deemed acceptable. Other conditions for rejecting measurements can relate to stability or reproducibility of the humidity measurement.

Figure 5:
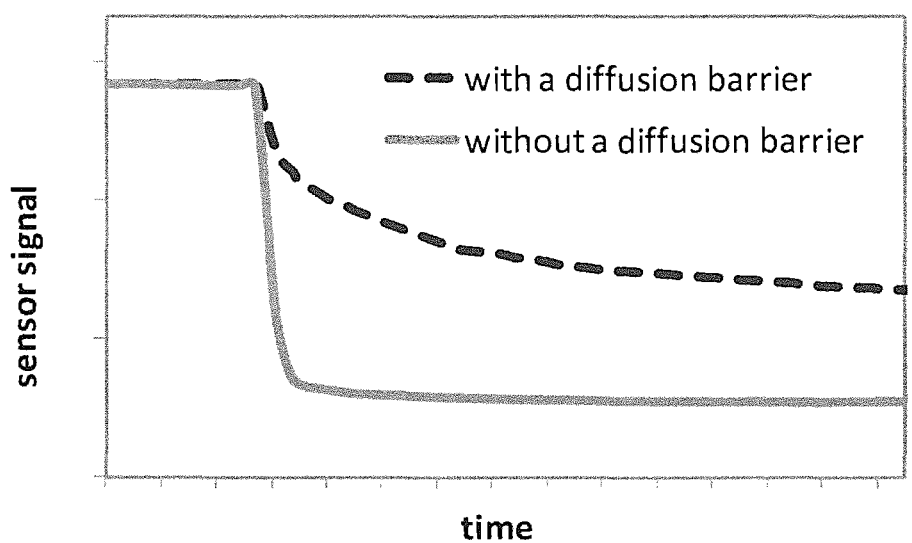
FIG. 5 illustrates the effect a small opening has on the measurement of a chemical sensor located behind it.

In addition to the compensation for dilution by the ambient as described above, the compensator of the present invention is also configured to compensate for the effects of a small opening which restricts diffusion between the mouth or nose of the user and the location of the chemical sensor. The effect of the diffusion is illustrated by FIG. 5.

The figure shows the curves fitted to measurements of a chemical sensor in response to a pulse of air with 0.5 per mille BAC in either the absence (dashed curve) and in the presence (solid curve), respectively, of an opening behind which the sensor is located, within a restricted volume in the absence of the opening and with no restrictions on the volume the measured values represent the sample very accurately (dashed curve) with the resistance falling rapidly to a value representing the alcohol concentration of the sample. When however the sensor is located behind an opening and within a limited volume, the gas concentration changes much slower and the resistance drops to a value above the resistance of the free sensor.

Using a test geometry and an exponential fit the time to reach the final value increases by a factor of around 50 to 100 and the final value differs by about 100 percent.

To compensate for these distortions in the measuring process, she compensator applies a correction in accordance with equations [2]-[4], with $$Ci=\gamma Cmf(t) \qquad [2]$$

wherein the first function γ represents the balance between the diffusion of the measured component to the chemical sensor and its reduction or consumption due to a reaction at the sensor and wherein f(t) is a time dependent function representing geometrical constraints which approaches 1 at long time intervals. These functions can be derived for example from a mass balance equation and a diffusion model. Depending on the derivation, the functions can be represented for example by $$Ci=Cm(1/(1+Lk/SD))(1-\exp(-t/\tau)) \text{ with} \qquad [3]$$

$$\tau=LV/(SD+Lk)=LV/SD*(1/(1+Lk/SD)). \qquad [4]$$

Referring again to FIG. 2, the opening 206 is assumed for this example to have a diameter S of about 1 mm and the wall of the housing a thickness L of 2 mm, thus defining a throat section through which the air has to migrate to reach the chemical sensor 22. The volume of the duct 21 around the sensor is V. The reaction rate of the analyte at the surface of the chemical sensor is denoted by k as a measure of how fast the reaction at the sensor takes place and D is the diffusion coefficient of the component in air.

With these variables known the compensator 24 can correct at any instant the concentration Ci as measured within the duct to the value Cm outside the duct without waiting for an equilibrium state.

In a breath analyzer in accordance with the invention such a correction is important as the ambient air may change the concentration Cm faster than the time required to establish an equilibrium between Cm and Ci through the opening 206.

The above model neglects the effect of a forced air flow through the opening and thus works best for ducts which are fanless, i.e. without a ventilation device. Such a device creates a convection, which is not considered in the above model.

The compensator 24 is further capable and designed to compensate for the characteristic of individual sensors. This is seen as a useful element as the above described compensation methods can involve the use of two measurements as performed by different sensors. However such a compensation can be applied in principle for any two different sensors integrated into thp portable device, the outputs of which sensors need to be combined in a processing step.

Figure 6:
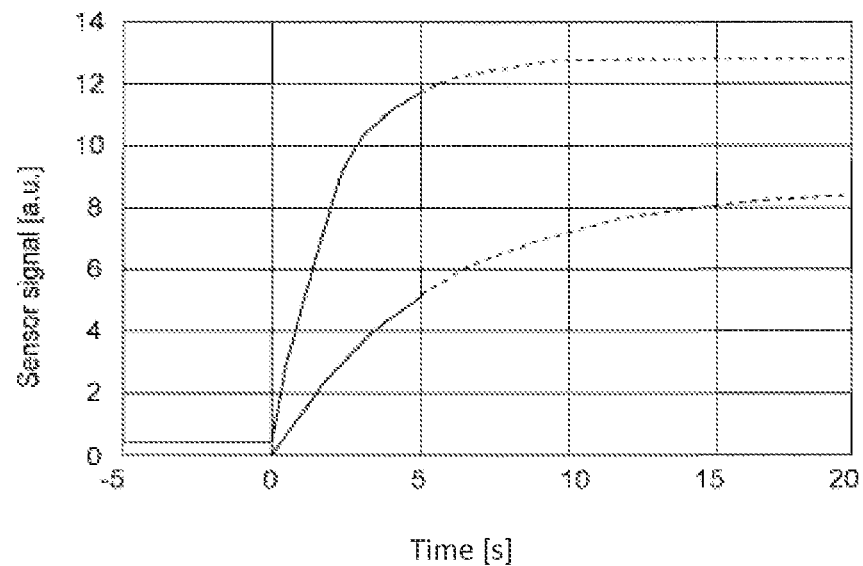
FIG. 6 and FIG. 7 illustrate the responses of two sensors before and after a compensation for the different response time, respectively.
Figure 7:
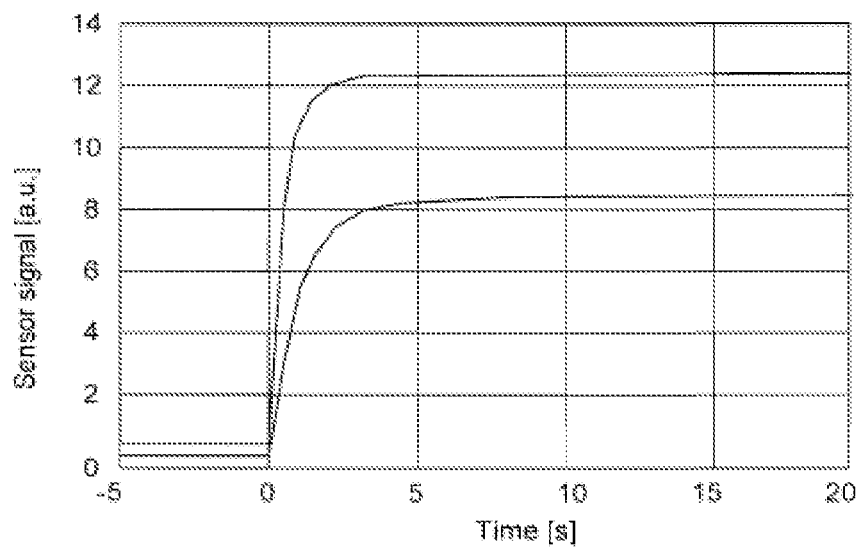

In FIGS. 6 and 7, the responses of two sensors are shown before and after a compensation for the different response time. In FIG. 6 it is illustrated how the two sensors react when exposed to the same sample. The solid part of the curves represents the measurements made in a time window of 0.5 seconds whilst the dashed part shows the further measurements signals, provided the measurements were continued for a longer time period. Both sensors would reach the asymptotic, accurate value outside the time window of 5 seconds, with the first sensor represented by the upper curve earlier than the second sensor represented by the lower curve.

To render both measurements comparable and hence suitable to a common processing, the measurements made within the first 5 seconds are combined with the known response of the sensors to generate a representation of the measurement on a common but shortened time scale. As a result the curves of FIG. 7 represent measurement at a common time scale with the correct amplitude of each measurement at any given time. The time scale and hence the filter or transformation applied is in addition chosen such that the asymptotic, accurate value is reached with a time as allotted to the measurement. In the example shown the time of measurement is shortened from about 20 seconds to about 5 seconds. Methods such as described for example in the published United States patent application U.S. 2011/307208 can be used in order to model sensor responses and process joined measurements.

While there are shown and described presently preferred embodiments of the invention, it is to be understood that the invention is not limited thereto but may be otherwise variously embodied and practiced within the scope of the following claims. For example the functions and factors used for compensation as represented by equations [1]-[4] are used only to describe an implementation of the present invention in greater detail and can in practice be replaced by tables of stored values or other implementations suited for electronic devices. They can also be approximated by constant values in cases where such a basic compensation is deemed sufficient for the desired accuracy of the measurement.

The invention claimed is:

1. A portable electronic device, comprising:
   a breath analyzer comprising:
      a chemical sensor sensitive to the concentration of a component in a sample of exhaled breath of a user;
      an additional sensor; and
      a compensator,
   wherein:
      the chemical sensor and the additional sensor are enclosed in a housing of the portable electronic device, within an air duct of the portable electronic device, wherein said air duct comprises an opening to the exterior of the housing;
      the additional sensor is sensitive to conditions in the duct, behind the opening; and
      the compensator is connected to an output of each of the chemical sensor and the additional sensor;
   and wherein:
      the compensator is an electronic circuit or processing unit that is programmed, designed, adapted or configured to combine outputs from each of the chemical sensor and the additional sensor for compensating for the effect of variations in an amount of exhaled breath between a user and a location of the chemical sensor with the chemical sensor being integrated in the duct of the portable electronic device,
   wherein the compensator is further programmed, designed, adapted or configured to correct for dilution of exhaled breath by ambient air at the outside of the opening, based on outputs from the additional sensor that is sensitive to conditions in the duct, and
   wherein the compensator includes a compensation for different characteristics of different sensors.

2. The portable electronic device according to claim 1, wherein the additional sensor is further configured to determine one of: a humidity level, a carbon dioxide concentration, an oxygen concentration, a temperature, and an air flow, to correct for dilution of exhaled breath by ambient air at the outside of the opening.

3. The portable electronic device according to claim 1, wherein the compensator is further programmed, designed, adapted or configured to compensate for different time responses of different sensors of the breath analyzer.

4. The portable electronic device according to claim 1, wherein the compensator is further programmed, designed, adapted or configured to determine a ratio of signals from the additional sensor that are representative of changes in the humidity and signals from the additional sensor that are representative of changes in the component concentration, to correct for dilution of exhaled breath by ambient air at the outside of the opening.

5. The portable electronic device according to claim 1, wherein the compensator is further programmed, designed, adapted or configured to determine a value representative of the dew point to correct for dilution of exhaled breath by ambient air at the outside of the opening.

6. The portable electronic device according to claim 1, wherein the compensator is further programmed, designed, adapted or configured to derive values from measurement of ambient air made before or after a sampling of exhaled air to determine the compensation.

7. The portable electronic device according to claim 1, wherein the said component is one of: ethanol, acetone, hydrogen, methane, NO, CO, isoprene, and ammonia.

8. The portable electronic device according to claim 1, wherein the chemical sensor comprises a metal-oxide sensing material.

9. The portable electronic device according to claim 1, wherein the chemical sensor comprises: a metal-oxide sensing material: and a substrate including CMOS circuitry, wherein the metal-oxide sensing material is mounted onto and electrically connected to the substrate including CMOS circuitry.

10. The portable electronic device according to claim 1, wherein the portable electronic device is selected from the group consisting of a mobile phone, a handheld computer, an electronic reader, a tablet computer, a game controller, a pointing device, a photo camera, a video camera, a digital music player, a wrist watch, a key fob, a head set, and a computer peripheral.

* * * * *